(12) United States Patent
Gerberding

(10) Patent No.: US 6,790,224 B2
(45) Date of Patent: Sep. 14, 2004

(54) MEDICAL DEVICES

(75) Inventor: Brent C. Gerberding, Sunnyvale, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/067,722

(22) Filed: Feb. 4, 2002

(65) Prior Publication Data
US 2003/0149466 A1 Aug. 7, 2003

(51) Int. Cl.⁷ .................................................. A61F 2/06
(52) U.S. Cl. ..................... 623/1.12; 623/1.23; 623/1.13
(58) Field of Search ............................ 623/1.11, 1.12, 623/1.13, 1.23, 1.42, 1.43, 1.34, 1.1; 606/108

(56) References Cited

U.S. PATENT DOCUMENTS

| | | | |
|---|---|---|---|
| 4,950,227 A | | 8/1990 | Savin et al. |
| 5,336,234 A | | 8/1994 | Vigil et al. |
| 5,360,401 A | | 11/1994 | Turnland |
| 5,403,341 A | * | 4/1995 | Solar ........................... 606/198 |
| 5,549,635 A | | 8/1996 | Solar |
| 5,674,242 A | | 10/1997 | Phan et al. |
| 5,755,769 A | | 5/1998 | Richard et al. |
| 6,063,112 A | * | 5/2000 | Sgro ........................... 623/1.12 |
| 6,168,617 B1 | | 1/2001 | Blaeser et al. |
| 6,168,619 B1 | | 1/2001 | Dinh et al. |
| 6,221,097 B1 | | 4/2001 | Wang et al. |
| 6,315,792 B1 | * | 11/2001 | Armstrong et al. ........ 623/1.23 |
| 6,432,129 B2 | * | 8/2002 | DiCaprio ................... 623/1.11 |
| 6,432,130 B1 | | 8/2002 | Hanson |
| 2002/0052640 A1 | * | 5/2002 | Bigus et al. ............... 623/1.11 |

FOREIGN PATENT DOCUMENTS

| | | |
|---|---|---|
| EP | 0 697 226 A1 | 2/1996 |
| EP | 0 732 087 A1 | 9/1996 |
| WO | WO 01/80780 A2 | 11/2001 |
| WO | WO 02/060345 A2 | 8/2002 |

OTHER PUBLICATIONS

PCT Search Report dated Jun. 3, 2003.
Heidner et al., U.S.S.N. 10/066,994, filed Feb. 4, 2002.

* cited by examiner

Primary Examiner—Corrine McDermott
Assistant Examiner—Thomas J Sweet
(74) Attorney, Agent, or Firm—Fish & Richardson, P.C.

(57) ABSTRACT

A medical device includes a catheter having an expandable balloon, an expandable endoprosthesis positioned on the balloon, and an expandable sleeve. The endoprosthesis has a first end and a second end, and the expandable sleeve extends over an end of the endoprosthesis and a portion of the balloon adjacent to the end of the endoprosthesis. The sleeve is configured to separate into a plurality of portions.

43 Claims, 6 Drawing Sheets

MEDICAL DEVICES

TECHNICAL FIELD

This invention relates to medical devices, such as endoprostheses.

BACKGROUND

Medical endoprostheses, such as stents, can be placed within the body to perform a function, such as maintaining open a body lumen, for example, a passageway occluded by a tumor or a blood vessel restricted by plaque. Other endoprostheses such as stent-grafts, or covered stents, can be used to substitute for or reinforce a lumen, such as the aorta or other blood vessels that have been weakened, e.g., by an aneurysm.

Endoprostheses can be delivered inside the body by a catheter that supports an endoprosthesis in a compacted or reduced-size form as the endoprosthesis is transported to a desired site. Upon reaching the site, the endoprosthesis is expanded, for example, so that it contacts the walls of the lumen.

The expansion mechanism may include forcing the endoprosthesis to expand radially. For example, the expansion mechanism can include the catheter carrying a balloon, which carries the endoprosthesis. The balloon can be inflated so as to deform and fix the expanded endoprosthesis at a predetermined position in contact with the lumen wall. The balloon can then be deflated, and the catheter removed.

SUMMARY

This invention relates to medical devices, such as endoprostheses.

In one aspect, the invention features a medical device including a catheter having an expandable balloon, an expandable endoprosthesis positioned on the balloon, and an expandable sleeve. The endoprosthesis has a first end and a second end, and the expandable sleeve extends over an end of the endoprosthesis and a portion of the balloon adjacent to the end of the endoprosthesis. The sleeve is configured to separate into a plurality of portions.

Embodiments of aspects of the invention may include one or more of the following features. The endoprosthesis includes a stent. The endoprosthesis has an outer surface, and the sleeve extends over or covers the outer surface of the endoprosthesis. The sleeve extends over the first and second ends of the endoprosthesis.

The balloon can include a tapered portion, and the sleeve can be attached to the tapered portion. The balloon can include a sleeve portion, and the sleeve can be attached to the sleeve portion. The sleeve can be attached to the catheter.

The sleeve can be a tubular member. The sleeve can be configured to separate into at least three portions. The sleeve can include a polymer, such as a silicone, a polyurethane, a latex, and a polyether amide. The sleeve can include a therapeutic agent. The sleeve can have a surface defining an opening. The sleeve can be configured to separate at a predetermined pressure. The sleeve can be configured to separate at a predetermined level of expansion of the balloon. The sleeve can include portions configured to move away from the endoprosthesis after the sleeve separates.

In another aspect, the invention features a medical device having a catheter including an expandable balloon, a stent positioned over the balloon, the stent having an outer surface, a first end, and a second end, and a sleeve extending over the outer surface and the first and second ends of the stent, the sleeve further extending over portions of the balloon adjacent to the ends of the stent. The sleeve includes a separation portion.

Embodiments of aspects of the invention may include one or more of the following features. The sleeve includes a polymer. The sleeve includes a therapeutic agent. The sleeve is attached to the catheter. The sleeve is a tubular member. The sleeve covers the outer surface of the stent.

The balloon can have a tapered portion, and the sleeve can be attached to the tapered portion. The balloon can have a sleeve portion, and the sleeve can be attached to the sleeve portion.

The separation portion can be perforated. The separation portion can have a thickness less than a thickness of the balloon. The separation portion can be over the stent and/or over the balloon.

The device can include a plurality of separation portions. The separation portions can be asymmetrically positioned along the catheter. The separation portions can be configured to separate under different or similar conditions.

In another aspect, the invention features a method including positioning a medical device having a catheter having an expandable balloon, an expandable endoprosthesis positioned on the balloon, the endoprosthesis having a first end and a second end, and an expandable sleeve extending over an end of the endoprosthesis and a portion of the balloon adjacent to the end of the endoprosthesis; and separating the sleeve into a plurality of portions.

Embodiments of aspects of the invention may include one or more of the following features. Separating the sleeve includes expanding the sleeve. The method includes separating the sleeve sequentially. The method includes separating the sleeve into three portions substantially simultaneously. The method includes separating the endoprosthesis and the sleeve from the catheter. The sleeve has an outer surface defining an opening, and the method further includes aligning the opening with an opening of a body lumen.

Embodiments may have one or more of the following advantages. The sleeve can prevent the ends of the endoprosthesis from contacting, e.g., snagging or cutting, the body lumen, thereby reducing damage to the lumen. The sleeve can have a smooth, relatively low friction outer surface to provide the medical device with good insertion and tracking during use. The sleeve can include a drug that is released in the body lumen after the endoprosthesis and sleeve are delivered. Manufacturing of the sleeve can be relatively simple, with relatively low risk of contamination or damage to the sleeve.

Other features and advantages of the invention will be apparent from the description of the preferred embodiments thereof and from the claims.

DETAILED DESCRIPTION

Figure 1:
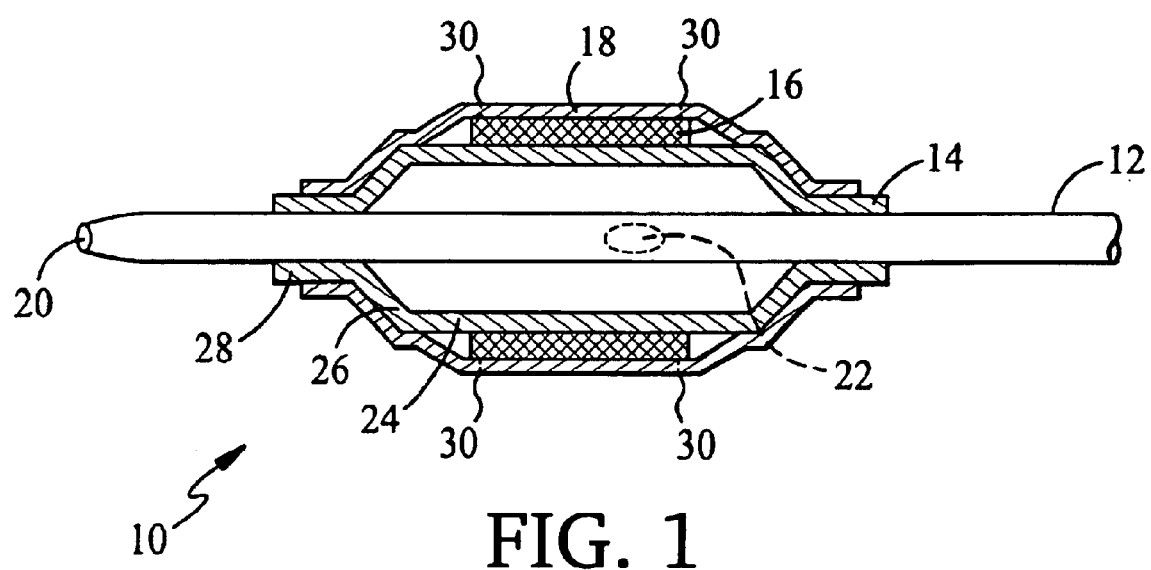
FIG. 1 is a cross sectional, schematic view of an embodiment of a medical device.

Referring to FIG. 1, a medical device 10 includes a catheter 12, a balloon 14 attached to the catheter, an endoprosthesis 16 positioned over the balloon, and an expandable sleeve 18 positioned over the endoprosthesis. Catheter 12 is a balloon catheter having a longitudinally extending guide wire lumen 20 for positioning the catheter, and a port 22 for inflating and deflating balloon 14. Balloon 14 has a body portion 24, tapered or conical portions 26 adjacent to the body portion, and sleeve portions 28 at the ends of the balloon. Sleeve portions 28 are attached to catheter 12, e.g., by laser bonding. Endoprosthesis 16, here, a stent, is crimped on balloon 14. Sleeve 18 is a tubular member that covers endoprosthesis 16, extends over body portion 24 and tapered portions 26, and is attached to sleeve portions 28 of balloon 14.

Sleeve 18 includes separation portions 30 extending circumferentially around the sleeve near the ends of endoprosthesis 16. Separation portions 30 are configured to separate under a predetermined condition during delivery of endoprosthesis 16. For example, separation portions 30 can tear, break away, or otherwise fail at a predetermined pressure that is applied to sleeve 18, and/or at a predetermined expansion and/or elongation of the sleeve. As a result, after endoprosthesis 16 is delivered, portions of sleeve 18 attached to balloon 14 (here, the distal and proximal ends of the sleeve) remain attached to catheter 12; while the remaining portion of the sleeve separated by separation portions 30 (here, the middle portion of the sleeve) detaches from the catheter and is delivered to the site with the endoprosthesis.

Figure 2A:
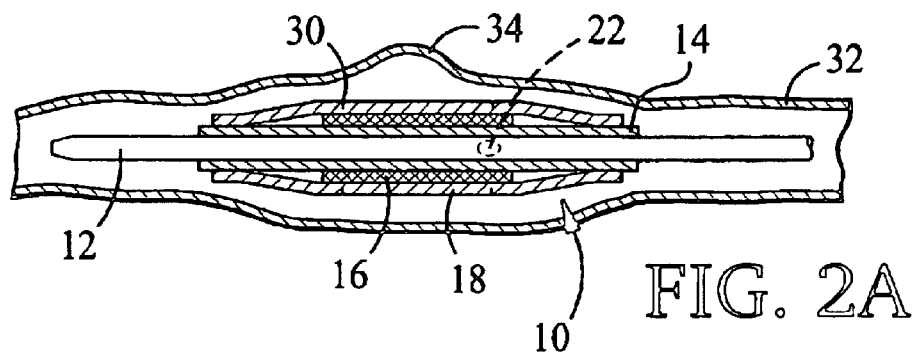
FIGS. 2A, 2B, 2C, and 2D are illustrations showing an embodiment of a method of using the medical device of FIG. 1.

FIGS. 2A–2D show an embodiment of a method of using device 10, here, to deliver endoprosthesis 16 and sleeve 18 to reinforce a blood vessel 32 that has been weakened by an aneurysm 34. Device 10 is positioned at a delivery site, for example, by passing an emplaced guide wire through guide wire lumen 20 and using fluoroscopic techniques (FIG. 2A). Balloon 14 is deflated to provide device 10 with a relatively low and compact profile. Since sleeve 18 covers the ends of endoprosthesis 16, the ends of the endoprosthesis are prevented from contacting, e.g., snagging or cutting, vessel 32. As a result, damage to the vessel is reduced. Sleeve 18 can also provide a relatively low friction or lubricious exterior for endoprosthesis 16 and balloon 14, which can enhance delivery, e.g., insertion and/or tracking, of device 10.

Figure 2B:
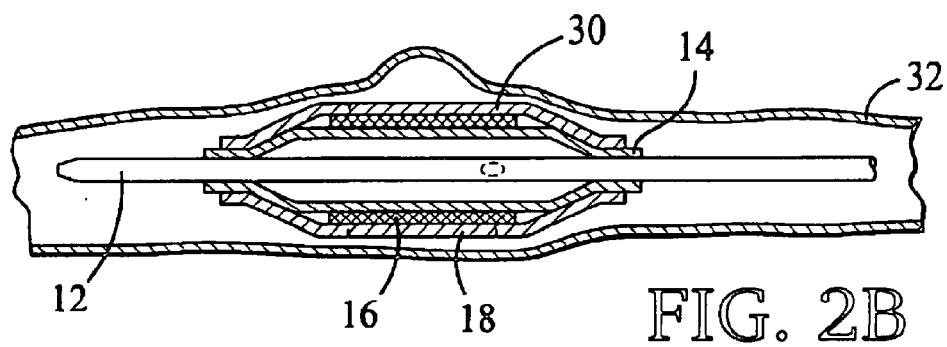
Figure 2C:
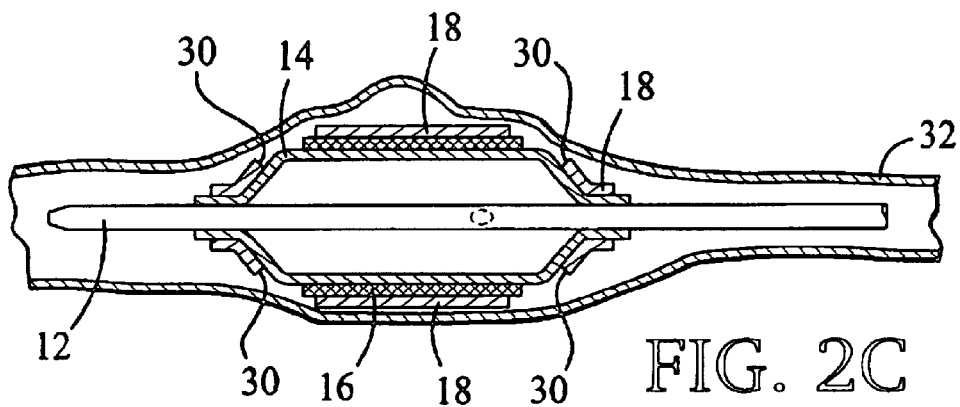
Figure 2D:
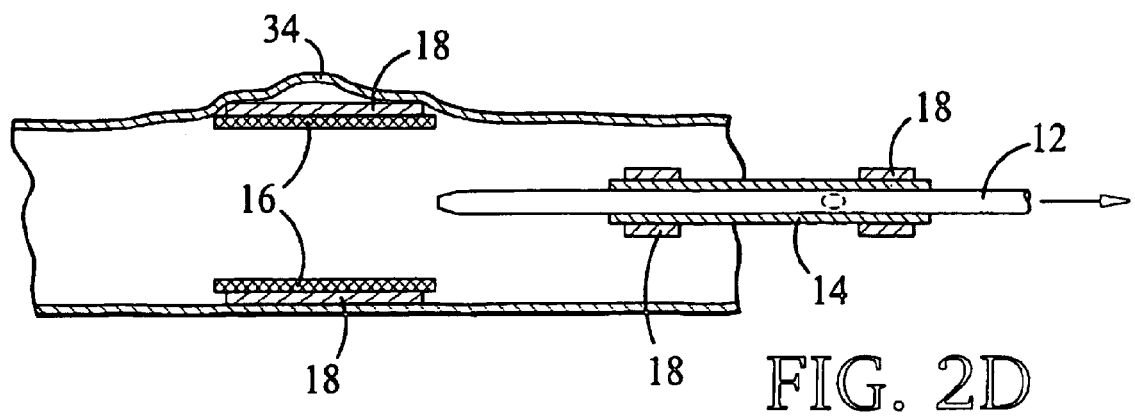

At the delivery site, balloon 14 is expanded, such as by flowing a fluid, e.g., a gas or a liquid, through port 22 and into the interior of the balloon (FIG. 2B). At a predetermined condition, e.g., pressure or expansion, separation portions 30 separate (FIG. 2C). As balloon 14 is continued to be expanded, portions of sleeve 18 attached the balloon remain attached, while the remaining portions are delivered to the site along with endoprosthesis 16. Balloon 14 continues to be expanded to a predetermined position, e.g., until endoprosthesis 16 and/or sleeve 18 contacts vessel 32. Balloon 14 is then deflated, and catheter is 12 is withdrawn (FIG. 2D).

Sleeve 18 can be made of any material that is expandable and relatively biocompatible. In some embodiments, sleeve 18 is made of a polymer, such as a biocompatible polymer and/or a thermoplastic polymer. Examples of suitable polymers include fluoropolymers, e.g., polytetrafluoroethylene; polyolefins, e.g., high density polyethylene; silicones; polyurethanes; latex; polyimides; or polyether amides. In certain embodiments, the material of sleeve 18 can be selected such that, after sleeve separation, portions of the sleeve attached to the catheter move, e.g. curl, slide, or roll, away from endoprosthesis 16 and/or contract about balloon 14 to facilitate deflation and folding of the balloon, and removal of device 10. In some embodiments, sleeve 18 includes a lubricant to enhance delivery of device 10. Examples of sleeve materials and lubricants, including methods of making a sleeve, are described in U.S. Pat. Nos. 6,221,097, 5,403,341, 5,108,416, 5,944,726, 5,968,069, and 4,950,227, hereby incorporated by reference in their entirety. Sleeve 18 can be made of multiple materials or include portions of different materials. For example, end portions of sleeve 18 can be made of a first material, while the portion between the end portions is made of a second, different material.

The attachment of sleeve 18 and the formation of separation portions 30 are generally a function of a desired separation characteristic(s). The separation characteristics include, for example, the conditions under which separation portions 30 separate, e.g., when the sleeve portions separate, where sleeve 18 separates along its length, and/or how the separation portions separate, e.g., sequentially or relatively simultaneously. In some embodiments, separation portions 30 separate at a pressure at or below a nominal pressure of balloon 14, or before the ends of sleeve 18 have exceeded the elastic limit of their elongation.

Referring again to FIG. 1, sleeve 18 is generally attached so that it can be expanded and controllably separated. In general, sleeve 18 can be configured to separate any time between when balloon 14 is expanded and when the sleeve and endoprosthesis 16 are delivered to their final position. Along the length of balloon 14, sleeve 18 can be attached at sleeve portions 28, tapered or conical portions 26, and/or body portion 24. In addition or alternatively, sleeve 18 can extend beyond the ends of sleeve portions 28 and be attached to catheter 12. In some embodiments, the attachment of sleeve 18 is different along the length of balloon 14 and/or catheter 12. For example, the distal end of sleeve 18 can be attached to the distal tapered portion 26 of balloon 14, and the proximal end of the sleeve can be attached to the proximal sleeve portion 28 of the balloon. This attachment configuration may allow separation portions 30 to separate in a selected sequence so that, for example, the distal end of sleeve 18 separates and contacts vessel 32 before the proximal end of the sleeve separates. Sleeve 18 can be attached to device 10 by a variety of methods, such as laser bonding, using an epoxy, heat shrinking, or heat staking.

Figure 3A:
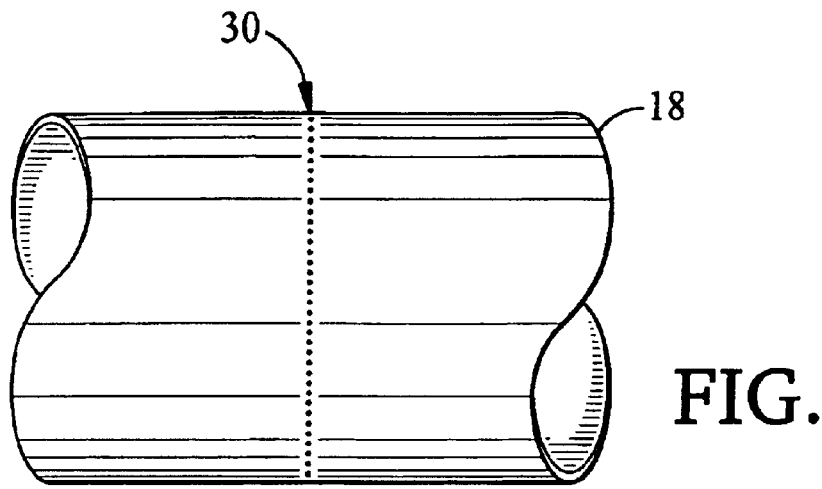
FIG. 3A is a detailed view of a portion of an embodiment of a sleeve.
Figure 3B:
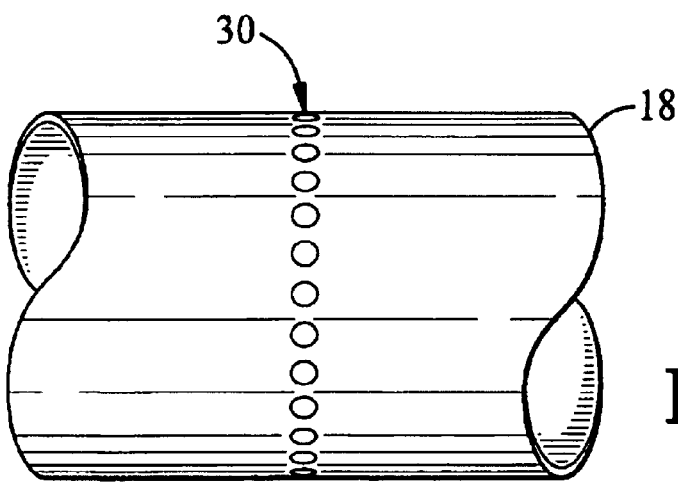
FIG. 3B is a detailed view of a portion of an embodiment of a sleeve.
Figure 3C:
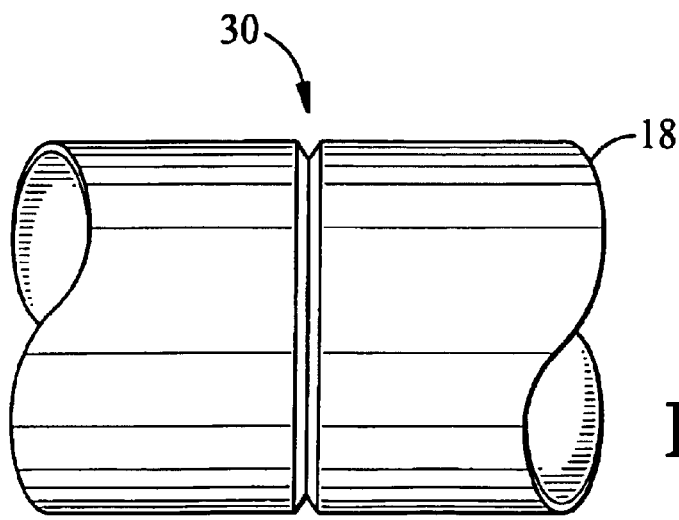
FIG. 3C is a detailed view of a portion of an embodiment of a sleeve.

Similarly, separation portions 30 are generally formed according to the desired separation characteristic(s). Separation portions 30 can be formed anywhere along the length of sleeve 18, such as over endoprosthesis 16, over body portion 24, over tapered portions 26, over sleeve portions 28, and/or over catheter 12. After separation, sleeve 18 can be longer or shorter than the length of endoprosthesis 16. As with the attachment of sleeve 18, separation portions 30 can be different from each other. For example, one separation portion 30 can be over endoprosthesis 16, while another separation portion is over balloon 14 (FIGS. 6A–6E). In certain embodiments, sleeve 18 includes more than two separation portions. For example, the distal end of sleeve 18 can have a series of spaced separation portions 30 configured to separate the distal end of the sleeve sequentially as balloon 14 is inflated. Separation portions 30 can be formed by removing portions of sleeve 18, for example, by mechanically weakening, thinning, perforating, or selectively drilling the sleeve with an excimer laser (FIGS. 3A and 3B), or by scribing (FIG. 3C). The amount of sleeve 18 that is removed can determine how easily separation portions 30 separate. In some embodiments, the material used for separation portions 30 can be selected to be relatively weaker than other portions of sleeve 18 to provide preferential separation at the separation portions. As a result, sleeve 18 can be formed with uniform thickness along its length. Separation portions 30 can be narrow, e.g., a line extending circumferentially around sleeve 18, or relatively wide.

In certain embodiments, sleeve 18 includes, e.g., is embedded, with a therapeutic agent or a pharmaceutically active compound for release at the delivery site. For example, the drug can be incorporated into sleeve 18 by passive diffusion after fabrication of the sleeve, or by compounding the drug with the sleeve material. In some cases, by forming sleeve 18 as one member having a therapeutic agent, contamination of the sleeve is reduced, relative to, for example, a device having a drug-loaded sleeve made of a first polymer covering endoprosthesis 16, and separate sleeve portions made of a different, second polymer covering the ends of the endoprosthesis. Manufacturing of a one-member sleeve 18 can also be relatively simple and cost efficient. Since manufacturing can be relatively simple, the risk of damaging sleeve 18 can be reduced.

Examples of therapeutic agents or pharmaceutically active compounds include anti-thrombogenic agents, antioxidants, anti-inflammatory agents, anesthetic agents, anticoagulants, and antibiotics. Other examples of therapeutic agent are described in U.S. Pat. No. 5,674,242, hereby incorporated by reference.

Examples of catheter 12, balloon 14, and endoprosthesis 16 are described in incorporated-by-reference U.S. Pat. No. 4,960,227. An example of an endoprosthesis is a stent formed of a filament, e.g., a metal wire, configured into a tube.

Other Embodiments

Figure 4:
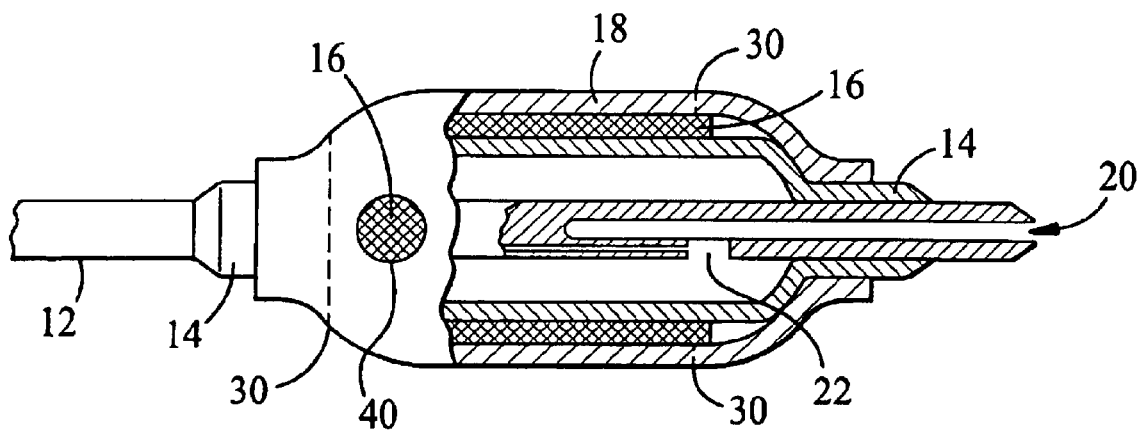
FIG. 4 is a partially cut-away view of an embodiment of a medical device.
Figure 5:
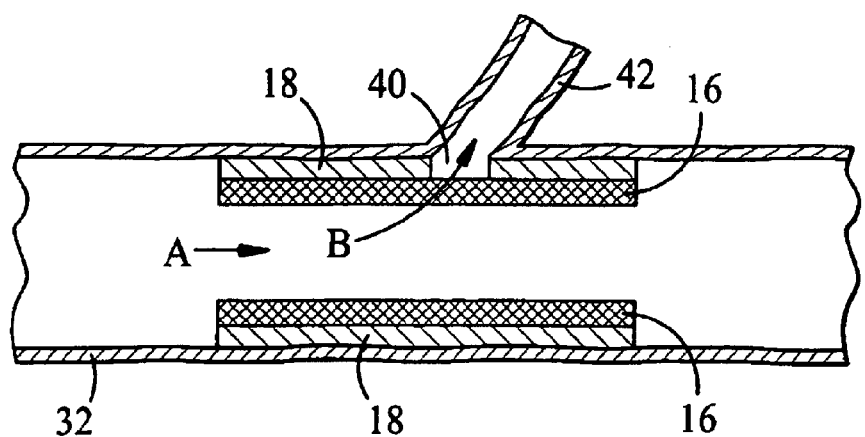
FIG. 5 is a cross sectional, schematic view of an embodiment of a medical device.
Figure 6A:
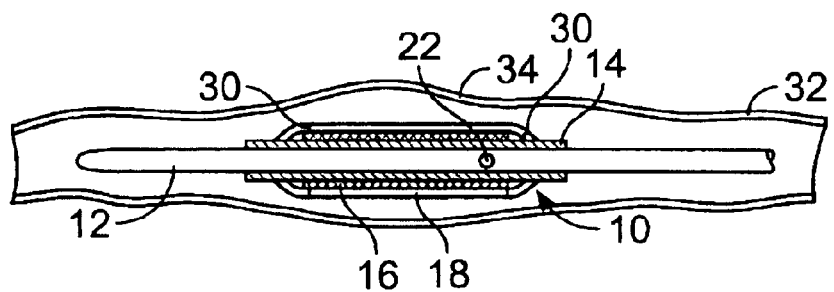
FIGS. 6A, 6B, 6C, 6D, and 6E are illustrations of an embodiment of a method of using another medical device.
Figure 6B:
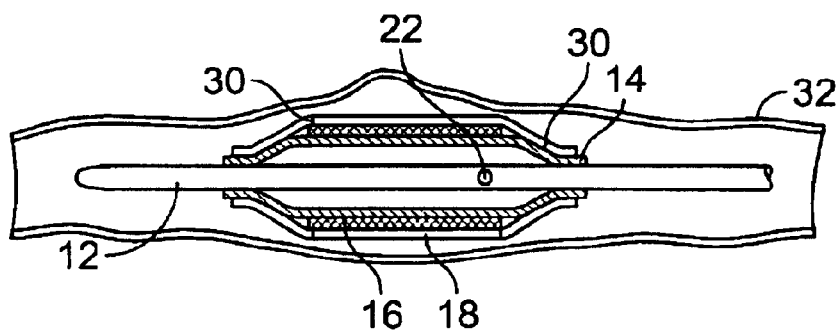
Figure 6C:
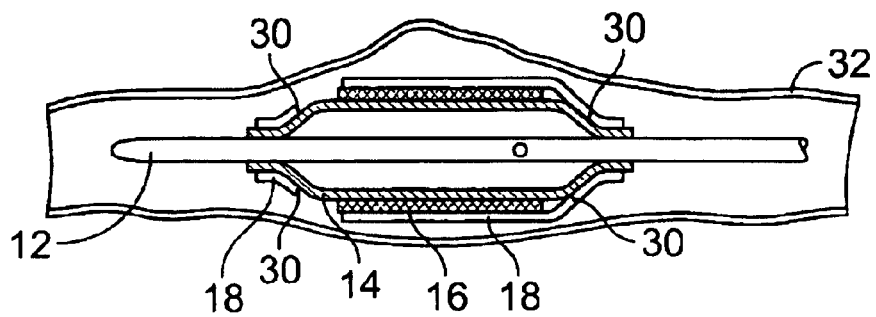
Figure 6D:
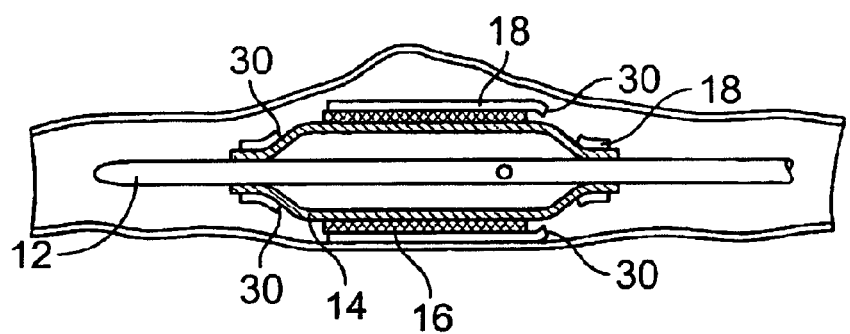
Figure 6E:
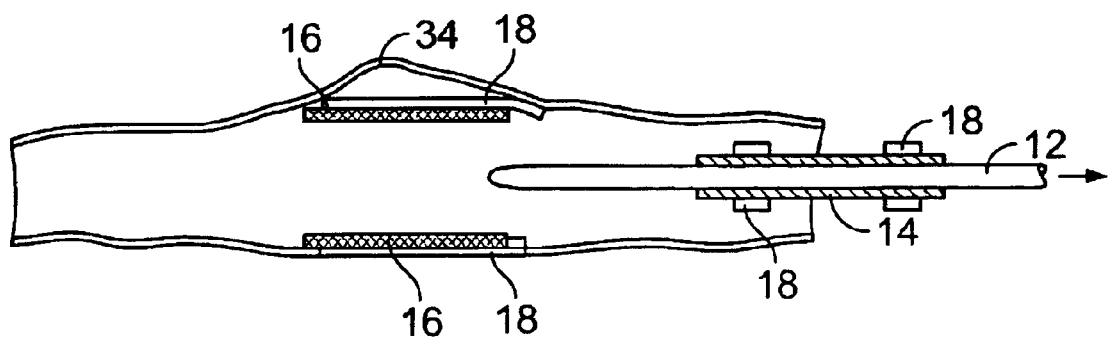

Referring to FIGS. 4 and 5, sleeve 18 can include one or more openings 40 on its side surface. Sleeve 18 can be used in a portion of vessel 32 having a side or branching vessel 42 in which opening 40 provides fluid communication between vessel 32 and vessel 42. As a result, fluid can flow through vessel 32 (via the lumen of endoprosthesis 16, arrow A) and through vessel 42 (via opening 40, arrow B). The dimensions and location of opening 40 on sleeve 18 can be determined by first evaluating the structure of the delivery site using fluoroscopic techniques, and tailoring the opening according to the determined structure. In some embodiments, sleeve 18 includes multiple openings 40 to provide fluid flow to multiple branching vessels.

In other embodiments, sleeve 18 extends and covers only one end of endoprosthesis 16, such as the distal end or the proximal end.

Separation portions 30 can be formed during delivery of endoprosthesis 16 or in situ. For example, balloon 14 can include cutting elements extending circumferentially around the balloon that cut sleeve 18 as the balloon is expanded, thereby separating the sleeve. Examples of cutting elements are described in U.S. Pat. No. 5,336,234, hereby incorporated by reference. Separation portions 30 can be formed chemically. For example, separation portions 30 can be formed of a material that, upon exposure to bodily fluids, e.g., blood, reacts, e.g., degrades or weakens, thereby allowing the separation portions to separate. Examples of materials are described in U.S. Pat. No. 5,443,495, hereby incorporated by reference.

Endoprosthesis 16 can be a self-expanding device or a device that is self-expanding and balloon-expandable. Endoprosthesis 16 can be embedded into sleeve 18. Sleeve 18 can completely encapsulate endoprosthesis 16. Device 10 can include radiopaque agent(s) or marker(s), for example, in the endoprosthesis, balloon, catheter, and/or sleeve.

In other embodiments, a sheath covers sleeve 18 and endoprosthesis 16, e.g., a self-expanding stent, carried on a catheter. During use, the sheath is retracted, allowing endoprosthesis 16 to expand and to separate sleeve 18, thereby implanting the endoprosthesis and the sleeve. As a result, the sheath can be made of relatively thin and flexible material because the combined constraining forces of the sleeve and the sheath can be used to hold the endoprosthesis in an unexpanded state. Examples of a self-expandable endoprosthesis is described in U.S. Pat. No. 5,725,570, hereby incorporated by reference.

Other embodiments are within the claims.

What is claimed is:

1. A medical device, comprising:
a catheter comprising an expandable balloon;
an expandable endoprosthesis positioned on the balloon, the endoprosthesis having a first end and a second end, the endoprosthesis defining a lumen extending between the ends; and
an expandable sleeve extending over an end of the endoprosthesis and a portion of the balloon adjacent to the end of the endoprosthesis,
wherein the sleeve is configured to separate into a plurality of detached portions, and a detached portion of the sleeve has a surface defining an opening between the ends.

2. The device of claim 1, wherein the endoprosthesis comprises a stent.

3. The device of claim 1, wherein the sleeve extends over the first and second ends of the endoprosthesis.

4. The device of claim 1, wherein the endoprosthesis has an outer surface, and the sleeve extends over the outer surface of the endoprosthesis.

5. The device of claim 1, wherein the endoprosthesis has an outer surface, and the sleeve covers the outer surface of the endoprosthesis.

6. The device of claim 1, wherein the balloon comprises a tapered portion, and the sleeve is attached to the tapered portion.

7. The device of claim 1, wherein the balloon comprises a sleeve portion, and the sleeve is attached to the sleeve portion.

8. The device of claim 1, wherein the sleeve is attached to the catheter.

9. The device of claim 1, wherein the sleeve is a tubular member.

10. The device of claim 1, wherein the sleeve is configured to separate into at least three portions.

11. The device of claim 1, wherein the sleeve comprises a polymer.

12. The device of claim 11, wherein the polymer is a material selected from a group consisting of a silicone, a polyurethane, a latex, and a polyether amide.

13. The device of claim 1, wherein the sleeve comprises a therapeutic agent.

14. The device of claim 1, wherein the sleeve is a tubular member having a lateral opening.

15. The device of claim 1, wherein the sleeve is configured to separate at a predetermined pressure.

16. The device of claim 1, wherein the sleeve is configured to separate at a predetermined level of expansion of the balloon.

17. The device of claim 1, wherein the sleeve includes portions configured to move away from the endoprosthesis after the sleeve separates.

18. The device of claim 1, wherein the endoprosthesis is embedded in the sleeve.

19. A medical device, comprising:
a catheter comprising an expandable balloon;
a stent positioned over the balloon, the stent having an outer surface, a first end, and a second end; and
a sleeve extending over the outer surface and the first and second ends of the stent, the sleeve further extending over portions of the balloon adjacent to the ends of the stent,
wherein the sleeve comprises a plurality of separation portions extending along portions of the circumference of the sleeve, the separation portions being configured to separate under different conditions.

20. The device of claim 19, wherein the sleeve comprises a polymer.

21. The device of claim 19, wherein the sleeve comprises a therapeutic agent.

22. The device of claim 19, wherein the balloon has a tapered portion, and the sleeve is attached to the tapered portion.

23. The device of claim 19, wherein the balloon has a sleeve portion, and the sleeve is attached to the sleeve portion.

24. The device of claim 19, wherein the sleeve is attached to the catheter.

25. The device of claim 19, wherein the separation portion is perforated.

26. The device of claim 19, wherein the separation portion has a thickness less than a thickness of the balloon.

27. The device of claim 19, wherein the separation portion is over the stent.

28. The device of claim 19, wherein the separation portion is over the balloon.

29. The device of claim 19, wherein the separation portions are asymmetrically positioned along the catheter.

30. The device of claim 19, wherein the sleeve is a tubular member.

31. The device of claim 19, wherein the sleeve covers the outer surface of the stent.

32. A method, comprising:
positioning a medical device comprising
a catheter comprising an expandable balloon,
an expandable endoprosthesis positioned on the balloon, the endoprosthesis having a first end and a second end, and
an expandable sleeve extending over an end of the endoprosthesis and a portion of the balloon adjacent to the end of the endoprosthesis, the sleeve having a surface defining an opening;
separating the sleeve into a plurality of detached portions; and
aligning the opening with an end opening of a body vessel.

33. The method of claim 32, wherein separating the sleeve comprises expanding the sleeve.

34. The method of claim 32, comprising separating the sleeve sequentially.

35. The method of claim 32, comprising separating the sleeve into three portions substantially simultaneously.

36. The method of claim 32, further comprising separating the endoprosthesis and the sleeve from the catheter.

37. The method of claim 32, wherein the sleeve comprises an outer surface defining an opening, the method further comprising aligning the opening with an opening of a body lumen.

38. A medical device, comprising:
a catheter;
an expandable sleeve attached to the catheter; and
an expandable endoprosthesis between the catheter and the sleeve, the endoprosthesis having a first end and a second end, the endoprosthesis defining a lumen extending between the ends;
wherein the sleeve is configured to separate into a plurality of portions, and a separated portion of the sleeve has a surface defining an opening between the ends.

39. The device of claim 38, wherein the catheter comprises an expandable balloon, and the sleeve and the endoprosthesis are carried by the balloon.

40. The device of claim 38, wherein the endoprosthesis is self-expandable.

41. The device of claim 38, wherein the sleeve covers the endoprosthesis.

42. The device of claim 38, wherein the endoprosthesis comprises ends, and the sleeve covers the ends of the endoprosthesis.

43. The device of claim 38, wherein the sleeve is a tubular member.

* * * * *